(12) United States Patent
Solomon et al.

(10) Patent No.: US 7,824,359 B2
(45) Date of Patent: Nov. 2, 2010

(54) BIOINJECTION DEVICE

(76) Inventors: Clifford T. Solomon, 18318 Brick Store Rd., Hampstead, MD (US) 21074; Theodore C. Solomon, 18318 Brick Store Rd., Hampstead, MD (US) 21074

( * ) Notice: Subject to any disclaimer, the term of this patent is extended or adjusted under 35 U.S.C. 154(b) by 0 days.

(21) Appl. No.: 12/458,779

(22) Filed: Jul. 22, 2009

(65) Prior Publication Data
US 2010/0022952 A1    Jan. 28, 2010

Related U.S. Application Data

(60) Provisional application No. 61/129,849, filed on Jul. 24, 2008.

(51) Int. Cl.
*A61M 31/00* (2006.01)
(52) U.S. Cl. .............. 604/57; 604/61; 604/63
(58) Field of Classification Search ......... 604/134–136, 604/138, 139, 157, 59–63; 606/92–95, 99, 606/100, 86 R; 623/17.12
See application file for complete search history.

(56) References Cited

U.S. PATENT DOCUMENTS

| | | | |
|---|---|---|---|
| D261,425 S | 10/1981 | Bruhn | |
| 4,338,925 A | 7/1982 | Miller | |
| 4,405,249 A | 9/1983 | Scales | |
| 4,518,384 A * | 5/1985 | Tarello et al. | 604/61 |
| 4,546,767 A | 10/1985 | Smith | |
| 4,815,454 A | 3/1989 | Dozier, Jr. | |
| 5,052,243 A | 10/1991 | Tepic | |
| 5,281,197 A * | 1/1994 | Arias et al. | 604/57 |
| 5,312,333 A * | 5/1994 | Churinetz et al. | 604/57 |
| 5,431,654 A | 7/1995 | Nic | |
| 6,309,395 B1 | 10/2001 | Smith et al. | |
| 6,439,439 B1 | 8/2002 | Rickard et al. | |
| 2006/0015067 A1 * | 1/2006 | Bates | 604/151 |
| 2007/0100449 A1 | 5/2007 | O'Neil et al. | |
| 2007/0255287 A1 | 11/2007 | Rabiner | |
| 2008/0009792 A1 | 1/2008 | Henniges et al. | |

* cited by examiner

*Primary Examiner*—Nicholas D Lucchesi
*Assistant Examiner*—Jenna Zhang
(74) *Attorney, Agent, or Firm*—Steptoe & Johnson LLP

(57) ABSTRACT

The bioinjection device has a housing including a pistol grip and an elongated barrel. A trigger is pivotally mounted to the housing. A plunger and needle are slidable between a first position in which the plunger and needle are slidably disposed in the barrel and a second position in which the plunger and needle extend from an opening in the end of the barrel. A retaining member is disposed about the opening at the end of the barrel. A spring-biased actuation mechanism connects the trigger with the plunger and needle. A membranous cartridge containing bone morphogenic protein, antibiotics, and/or other medication is loaded into the retaining member. A surgeon can inject the cartridge into a bone fracture or degenerative bone tissue during surgery to deliver the medicament directly to the affected site.

17 Claims, 10 Drawing Sheets

BIOINJECTION DEVICE

CROSS-REFERENCE TO RELATED APPLICATION

This application claims the benefit of U.S. Provisional Patent Application Ser. No. 61/129,849, filed Jul. 24, 2008.

BACKGROUND OF THE INVENTION

1. Field of the Invention

The present invention relates to devices for the delivery of pharmaceuticals, and particularly to a bioinjection device for delivering bone morphogenic protein, antibiotics, etc., directly to the site of a bone fracture, degenerative bone tissue or cartilage, etc., during the course of surgery in the form of a bioabsorbable matrix enclosed within a membrane cartridge.

2. Description of the Related Art

Bone is a living tissue and plays a structural role in the body. Disease and damage, however, is often difficult to treat in bones, due to their positioning within the soft tissues of the body. Bone consists of repeating Harvesian systems (concentric layers of lamellae deposited around a central canal containing blood vessels and nerves). The central canal is also known as the medullary cavity and is filled with bone marrow. Within the shaft of a long bone, many of these Harvesian systems are bundled together in parallel, forming a type of bone called compact bone, which is optimized to handle compressive and bending forces. In some bones, such as the metacarpals, for example, the bones themselves are hollow and contain little, if any, marrow. Near the ends of the bones, where the stresses become more complex, the Harvesian systems splay out and branch to form a meshwork of cancellous or spongy bone. Compact bone and cancellous bone differ in density, or how tightly the tissue is packed together.

Genetic or developmental irregularities, trauma, chronic stress, tumors, and disease can result in pathologies of bones. Some bone diseases that weaken the bones include, but are not limited to, osteoporosis, achondroplasia, bone cancer, fibrodysplasia ossificans progressiva, fibrous dysplasia, legg calve perthes disease, myeloma, osteogenesis imperfecta, osteomyelitis, osteopenia, osteoporosis, Paget's disease, and scoliosis. Weakened bones are more susceptible to fracture, and treatment to prevent bone fractures becomes important. Severe fractures, such as those that are open, multiple, or to the hip or back, are typically treated in a hospital. Surgery may be necessary when a fracture is open, severe, or has resulted in severe injury to the surrounding tissues. Severe fractures may require internal devices, such as screws, rods, or plates, to hold the bone in place or replace lost bone during the healing process.

In order to repair severe fractures, bone cement and the like is often applied within the fracture. However, other healing agents, such as antibiotics or bone morphogenic proteins, often need to be applied prior to cementing or performance of other operations on the bone. Due to the awkward positioning of bone fractures within other tissue, it is often quite difficult to properly apply medicaments and the like within the bone, particularly without damaging the tissue surrounding the bone. Thus, a bioinjection solving the aforementioned problems is desired.

SUMMARY OF THE INVENTION

The bioinjection device is directed towards a device for injecting or implanting a membrane-encased cartridge of pharmaceuticals and/or biologics, bone grafts, radioactive seeds and the like, in a bioabsorbable matrix or carrier directly into the site of a bone fracture, degenerative bone tissue or cartilage, or the like in the course of surgery. The cartridge may contain bone morphogenic protein, antibiotics, bone, bone substitute or the like.

The device includes a housing having an upper portion and a lower gripping portion. The lower gripping portion may be rotatable with respect to the upper portion and includes a handle member and a trigger member. The trigger member is pivotally secured to the handle member. Further, the upper portion of the housing has an open interior region formed therein.

A shaft is slidably mounted within the open interior region of the upper portion of the housing. The shaft has opposed forward and rear ends and is elongated along a longitudinal axis. Further, the shaft has a channel formed therethrough, also extending along the longitudinal axis from the forward end to the rear end.

At least one lever arm is pivotally mounted within the housing, with the at least one lever arm having opposed first and second ends. The first end of the lever arm is attached to the rear end of the shaft, and the second end is attached to the trigger member so that rotation of the trigger member with respect to the handle member drives sliding translation of the shaft with respect to the upper portion of the housing.

A needle is slidable within the channel formed through the shaft, the needle having opposed front and rear ends. The front end of the needle terminates in a relatively sharp point. The rear end thereof is attached to the at least one lever arm so that rotation of the trigger member with respect to the handle member drives forward sliding translation of the needle with respect to the upper portion of the housing and the shaft. Preferably, the at least one lever arm includes a pair of lever arms, including a first lever arm driving movement of the shaft and a second lever arm driving movement of the needle.

A retaining member has opposed front and rear ends. The front end is open and the rear end is attached to a forward portion of the upper portion of the housing. An opening is formed through the rear end of the retaining member and the forward portion of the upper portion so that the forward end of the shaft and the front end of the needle selectively and slidably project therethrough into an open interior region of the retaining member. The retaining member is preferably releasably attached to the forward portion of the upper portion of the housing.

A cartridge is releasably received within the open interior region of the retaining member. The cartridge includes an outer shell membrane and a medicament contained within the outer shell. The forward end of the shaft contacts the membrane so that actuation of the trigger member causes the shaft and the needle to slide forward, with the shaft pushing the cartridge out of the retaining member for deployment thereof into the bone fracture. As the shaft pushes the implant out of the retaining member, the needle pierces the outer shell membrane to release the medicament into the fracture or degenerative tissue.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
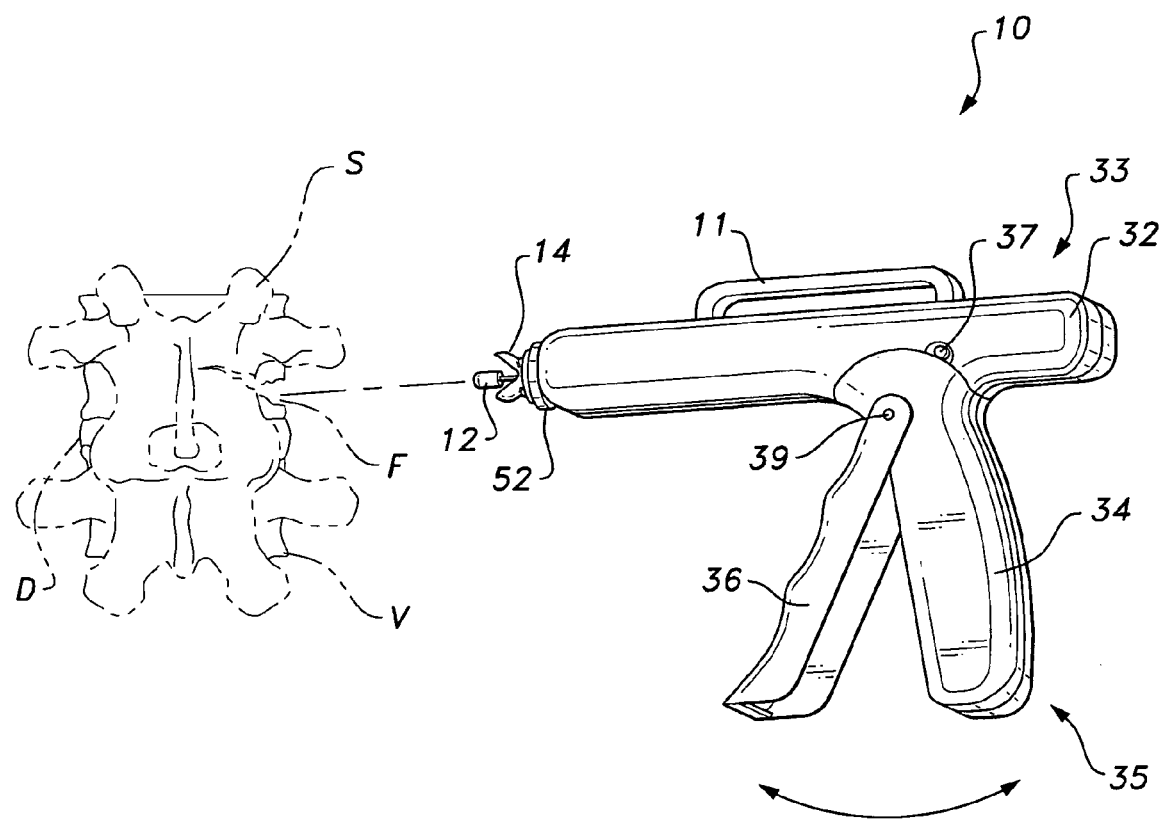
FIG. 1 is an environmental, perspective view of a bioinjection device according to the present invention.

The present invention relates to a bioinjection device 10. As shown in FIG. 1, device 10 is used to place a cartridge 12 into a fracture, degenerative tissue, or the like of a spinal segment S. The cartridge 12 contains a medicament (bone morphologic protein, antibiotics, or the like disposed in a bioabsorbable matrix or carrier) for the healing of the spinal segment S. It should be understood that spinal segment S, having vertebral bodies V, disc D and facet joint F, of FIG. 1 is shown for exemplary purposes only and is not intended to limit the type of bone or fracture that the cartridge 12 and device 10 may be used to treat.

Figure 2:
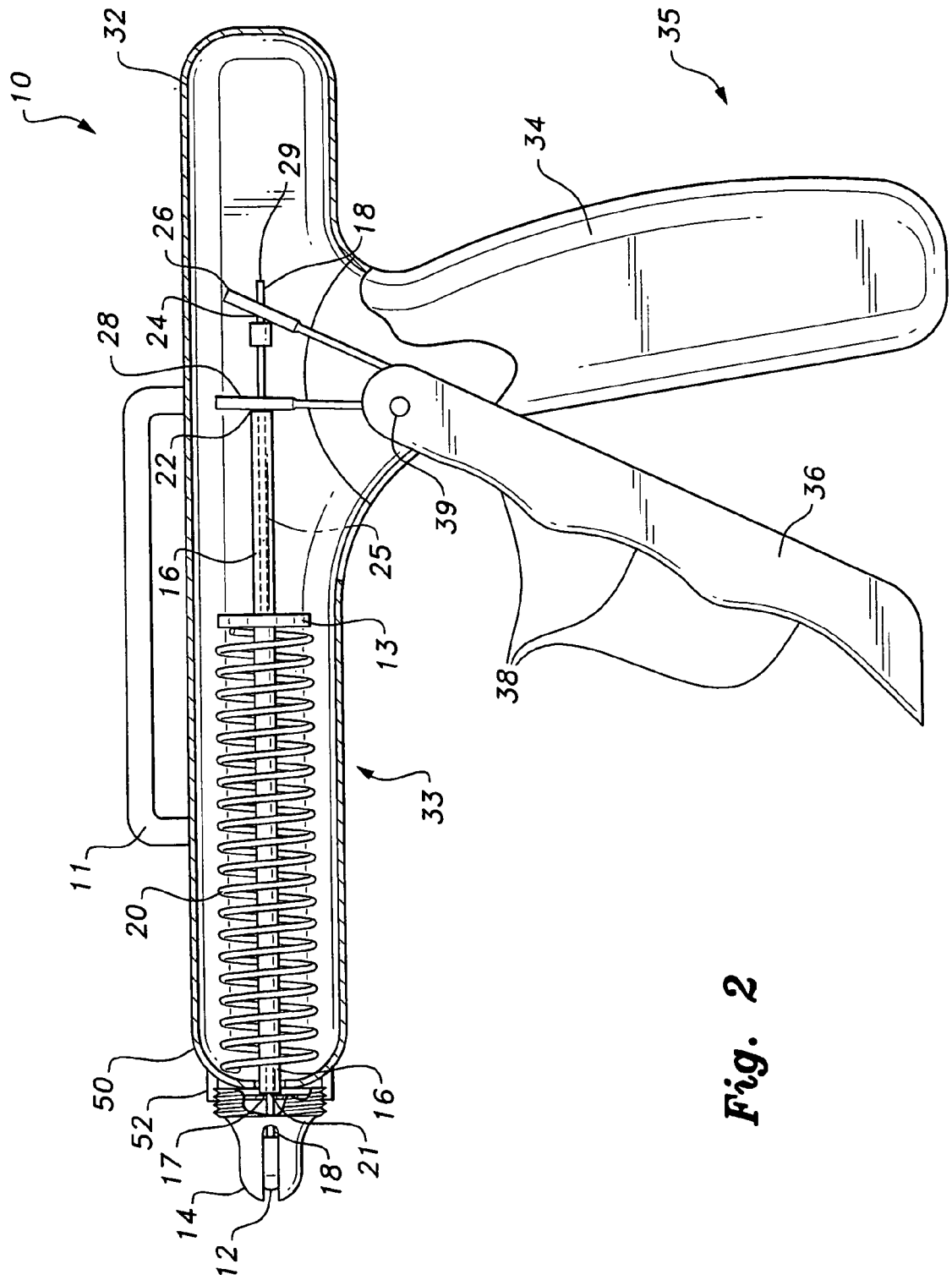
FIG. 2 is a side view of the bioinjection device according to the present invention, broken away and partially in section to show details thereof.

As best shown in FIGS. 1 and 2, the device 10 includes a housing 32 having a barrel-shaped upper portion 33 and a lower gripping portion 35. The lower gripping portion 35 may be rotatable with respect to the upper portion 33 and includes a pistol grip handle member 34 and a trigger member 36. The trigger member 36 is pivotally secured to the handle member 34 by a pivot pin 39 or the like. Trigger member 36 preferably has a plurality of finger receiving grooves or recesses 38 formed therein, as shown in FIG. 2, allowing for optimal gripping and actuation by the surgeon. Further, an upper gripping handle 11 may be mounted on an upper surface of housing 32, allowing the surgeon to better grip and secure tool 10 during the surgical operation.

As noted above, the lower portion 35, including both handle member 34 and trigger member 36, may be rotatable about pivot 37, allowing the lower gripping portion 35 to be rotated if necessary, depending upon the nature of the particular operation. The lower portion 35 may further be selectively locked in place with respect to the upper portion 33. Further, as shown in FIG. 2, the barrel-shaped upper portion 33 of housing 32 has an open interior region formed therein.

As shown in FIG. 2, a shaft 16 is slidably mounted within the open interior region of the upper portion 33 of the housing 32. The shaft has opposed forward and rear ends 21, 22, respectively, and is elongated along a longitudinal axis, as shown. Further, the shaft 16 has a longitudinally extending channel 25 formed therethrough, extending from the forward end 21 to the rear end 22. Shaft 16 is preferably resiliently or spring-biased with respect to housing 32. In the preferred embodiment, a stop 13, such as a disc, is mounted to a central portion of shaft 16, as shown in FIG. 2, with a spring 20 or other resilient element being biased between the stop 13 and the inner wall of forward portion 50 of housing 32.

At least one lever arm is pivotally mounted within housing 32 for the actuation of shaft 16. Preferably, the at least one lever arm includes a pair of lever arms with a first lever arm 28 driving movement of the shaft 16, and a second lever arm 26 driving movement of needle 18, as will be described in greater detail below. First lever arm 28 has opposed first and second ends, with the first end of first lever arm 28 being secured to the rear end 22 of shaft 16, and the second end being secured to the trigger member 36 so that rotation of the trigger member 36 with respect to the handle member 34 drives sliding translation of the shaft 16 with respect to the upper portion 33 of the housing 32.

Figure 4:
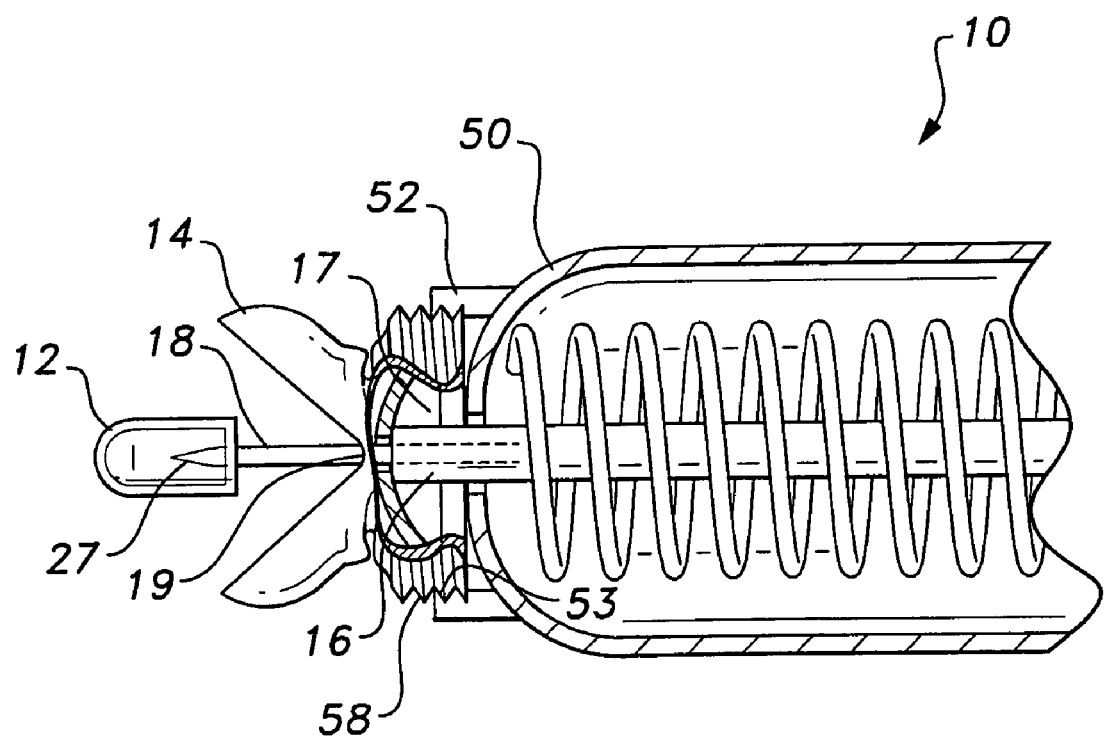
FIG. 4 is a partial side view in section of the bioinjection device, showing a cartridge extended from the device for injection or implantation.

Needle 18 is slidably received within the channel 25 formed through the shaft 16, with the needle 18 having opposed front and rear ends 27, 29, respectively (the front end or tip 27 of needle 18 is best shown in FIG. 4). The front end 27 of needle 18 is preferably formed as a relatively sharp point. The rear end 29 of needle 18 is secured at 24 to the second lever arm 26 so that rotation of trigger member 36 with respect to the handle member 34 drives forward sliding translation of the needle 18 with respect to the upper portion 33 of the housing 32 and also with respect to the shaft 16; i.e., actuation of trigger member 36 causes forward sliding of shaft 16 within the housing 32 and also forward sliding of needle 18 within the shaft 16.

A retaining member 14 is further provided, with the retaining member having opposed front and rear ends. As shown, retaining member 14 preferably forms a pair of gripping jaws for releasably holding implant 12. The front end thereof is open and the rear end thereof is secured to mounting member 52, which is fixed to a forward portion 50 of the upper portion 33 of the housing 32. The rear portion of retaining member 14 is preferably releasably attached to the mounting member 52 through use of any suitable releasable fastener. The rear portion may have threads 58 formed thereon, as best shown in FIG. 4, for reception by a threaded recess 53 formed in mounting member 52.

Further, an opening 19 is formed through the rear end of the retaining member 14, and a passage 17 is formed through the forward portion 50 of housing 32 so that the forward end 21 of shaft 16 and the front end 27 of the needle 18 selectively and slidably project therethrough into an open interior region of the retaining member 14.

Figure 3:
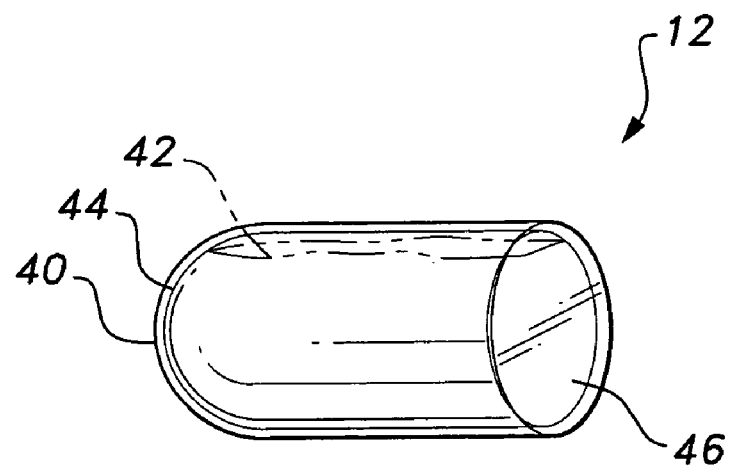
FIG. 3 is a perspective view of a membranous cartridge for use with a bioinjection device according to the present invention.

Cartridge 12 is releasably received within the open interior region of the retaining member 14. As best shown in FIG. 3, the cartridge 12 includes an outer shell membrane 40 and a medicament 42 contained within the outer shell 40. The medicament 42 may be a bone morphogenic protein, an antibiotic, or any other desired medicament for the healing of the bone, and may be disposed in a bioabsorbable matrix or carrier. The outer shell may be formed from hydroxyapatite calcium phosphate, or any other biodegradable material that will dissolve and/or fuse within the bone. Preferably, the rear end 46 of shell 40 is formed as a relatively thin membrane that can be pierced by tip 27 of needle 18. A further thin membrane 44 may be formed between the outer shell 40 and the medicament 42.

In use, the cartridge 12 is positioned within retaining member 14, as shown in FIG. 2, with the forward end 21 of shaft 16 contacting the rear surface 46 of the bone implant 12. Actuation of trigger member 36 causes the shaft 16 and the needle 18 to slide forward. Retaining member 14 is preferably formed from a flexible material, such as rubber, plastic or the like, so that forward movement of shaft 16 pushes the cartridge 12 out of the open front end of the retaining member 14 for deployment thereof into the bone fracture or other damaged or diseased area. As the shaft 16 pushes the cartridge 12 out of the retaining member 14, the tip 27 of needle 18 pierces the thin membrane 46 to release the medicament 42 into the fracture. The surgeon lodges the pierced cartridge 12 within fracture F or the degenerative bone tissue.

Figure 9:
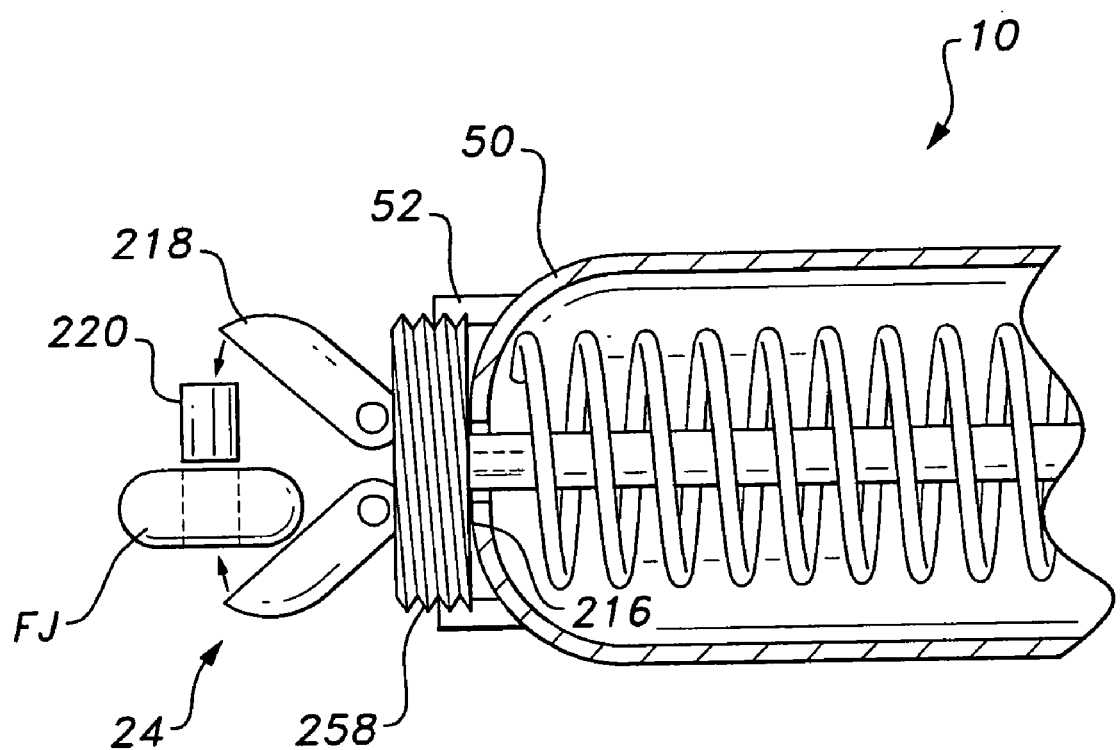
FIG. 9 is a side view of an alternative embodiment of the head of the bioinjection device according to the present invention.

In FIG. 9, retaining member or head 14 of FIG. 4 has been replaced by an alternative head 214, having a rear portion 216 with threads 258, similar to threaded connection 58 of FIG. 4. A pair of spring-biased jaws 218 are mounted to the rear portion 216, with one or both of the jaws 218 being adapted for releasably gripping a bone dowel 220 or the like for insertion into a facet joint FJ. In the embodiments of FIGS. 2 and 9, the heads 14, 214 and the shaft have relatively small sizes, allowing for placement within the facet joint, as noted above. However, it should be understood that the head and/or shaft may have any suitable size, dependent upon the site for placement of the cartridge. As will be described in detail below, a longer shaft and head may be necessary for injection of cartridges within a larger or longer bone, such as a tibia, and the shaft and head may be appropriately sized dependent upon the intended injection site.

Figure 6A:
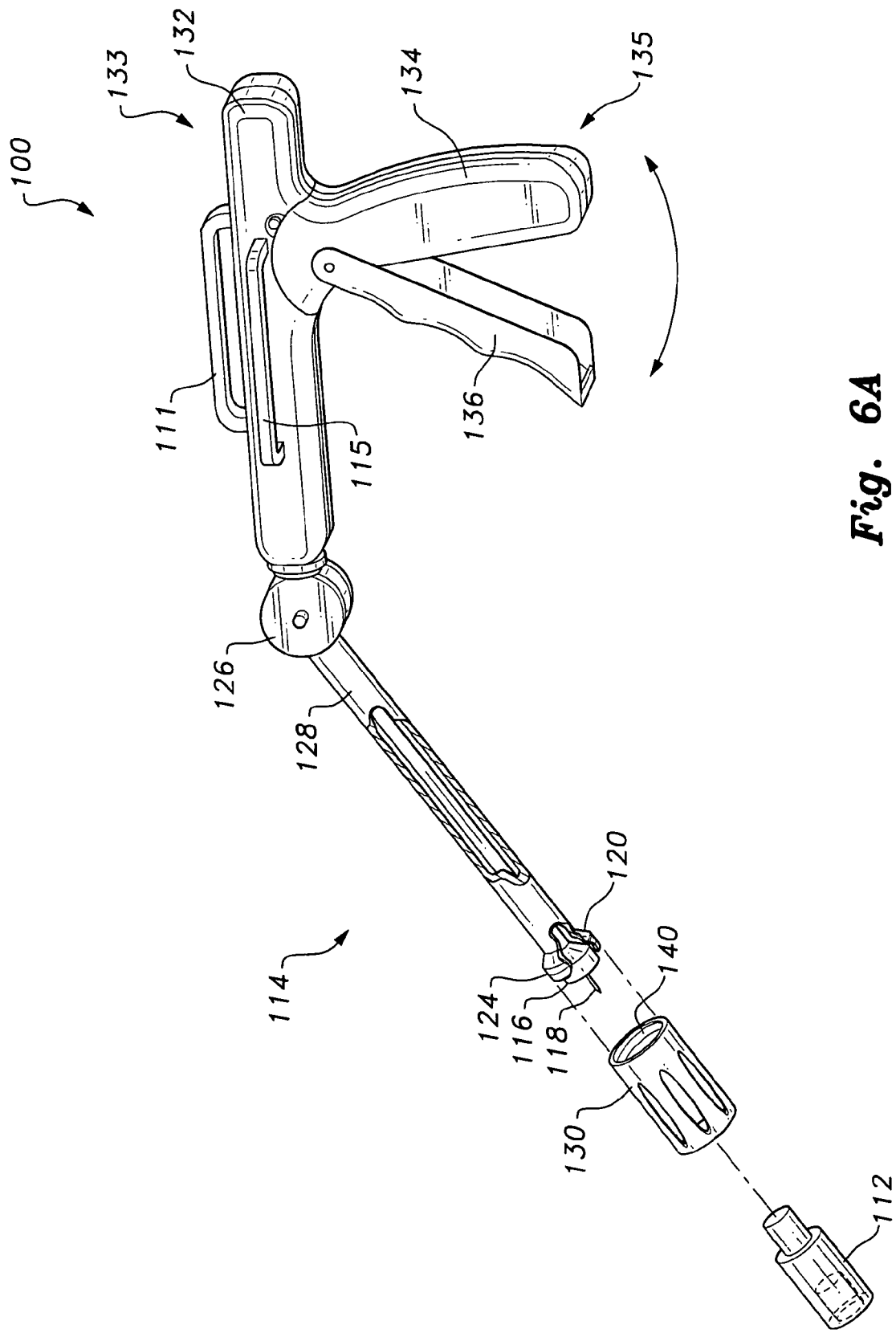
FIG. 6A is a perspective view of an alternative embodiment of the bioinjection device according to the present invention.

FIG. 6A illustrates an alternative embodiment of the bioinjection device. Bioinjection device 100 includes a housing 132 having upper and lower portions 133, 135, similar to that of the embodiment of FIGS. 1-4. Similarly, the lower portion 135 includes a handle member 134 and a trigger member 136, and the upper portion 133 has a handle 111 mounted thereon. Side handles 115 may also be mounted to upper portion 133, as shown, offering the surgeon a variety of gripping surfaces for differing angles of insertion during an operation. In the embodiment of FIG. 6A, an elongated tube 114 is mounted to the front end of barrel-shaped upper portion 133, allowing for the implanting of bone implants where immediate proximity of the surgeon's hands is not possible, such as in the implantation of implants 112 within channel C formed in tibia T of FIG. 8.

The elongated tube 114 includes an adjustable portion 126, allowing for angular adjustment of the tube 114 adjacent the front end of the upper portion 133 of housing 132. Adjustable portion may be a rotating and selectively locking disc member, as shown, or may be any other suitable angular adjustment device. A central region 128, preferably being solid and relatively non-flexible, is joined to the flexible portions 126 at one end thereof, and a head 120 is disposed at the other end of tube 114. Head 120 has an open outer end with external threads 124 formed therearound.

The retaining jaws 14 of the embodiment of FIGS. 1-5 are replaced in FIG. 6A by a cylindrical retaining member 130 having opposed open ends. Retaining member 130 is formed from a resilient, flexible material, similar to that described above with regard to jaws 14. Internal threads 140 are formed in one end of the retaining member 130 for releasable attachment to the head 120 via engagement with threads 124. It should be understood that retaining member 130 may be releasably secured to head 120 through any suitable releasable fastener.

An implant 112 is received within retaining member 130 for selective dispensing thereof. Similar to that described above with regard to the embodiment of FIGS. 1-5, an inner shaft 116, similar to shaft 16, extends through tube 114 and is shown in FIG. 6A slightly projecting from head 120. Shaft 116 preferably has a plunger-type shape, as shown, with a relatively wide outer face for pushing the wider implant 112. A needle 118, similar to needle 18, is housed within shaft 116. The alternative embodiment of FIG. 6B is substantially similar to that shown in FIG. 6A, but shaft 116 terminates in a covering head 117, which covers and surrounds the needle 118 and prevents the needle 118 from becoming caught in the implant 112. In operation, the user actuates trigger 136 to slide the shaft 116 and needle 118 forward so that the shaft 116 pushes the implant 112 out of retaining member 130 and needle 118 pierces the implant 112, as described above. When retaining member 130 is fixed to head 120, the head of plunger 116 will project out from retaining member 130 (when the trigger is compressed) by approximately one or two mm.

Figure 7:
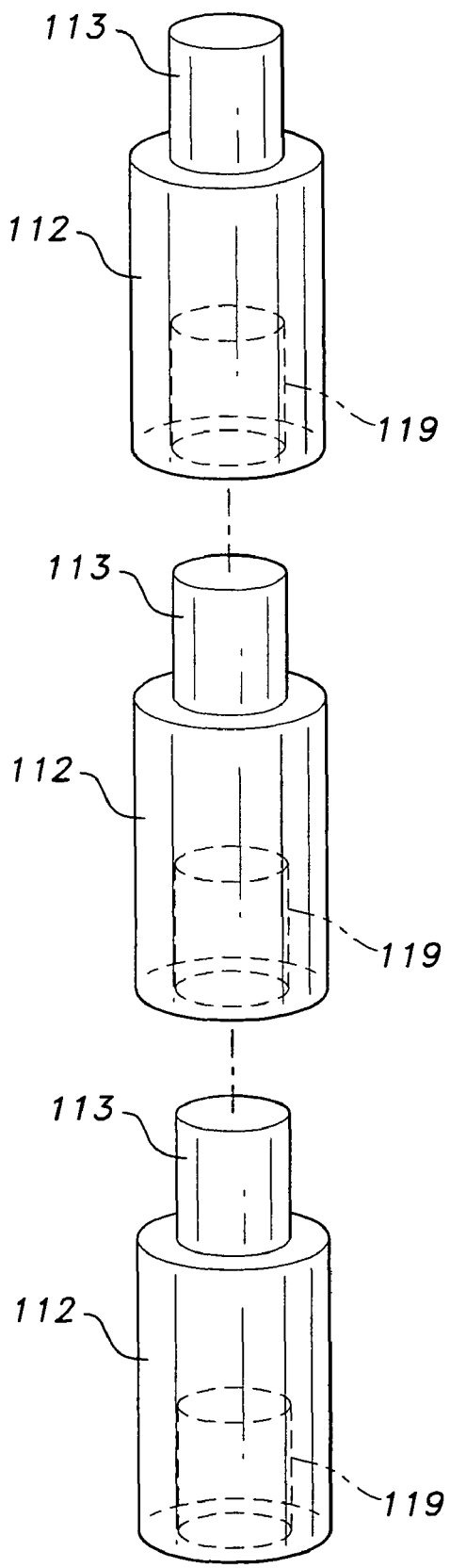
FIG. 7 is an exploded view of a plurality of alternative bone implants for use with the bioinjection device according to the present invention.

Implant 112 is preferably formed from materials similar to those described above with reference to implant 12. However, as best shown in FIG. 7, implant 112 preferably includes an upper projecting member 113 and a lower recess 119. As shown in FIG. 7, multiple implants 112 may be stacked through insertion of an upper projecting member 113 into a lower recess 119 of an adjacent implant.

Figure 5:
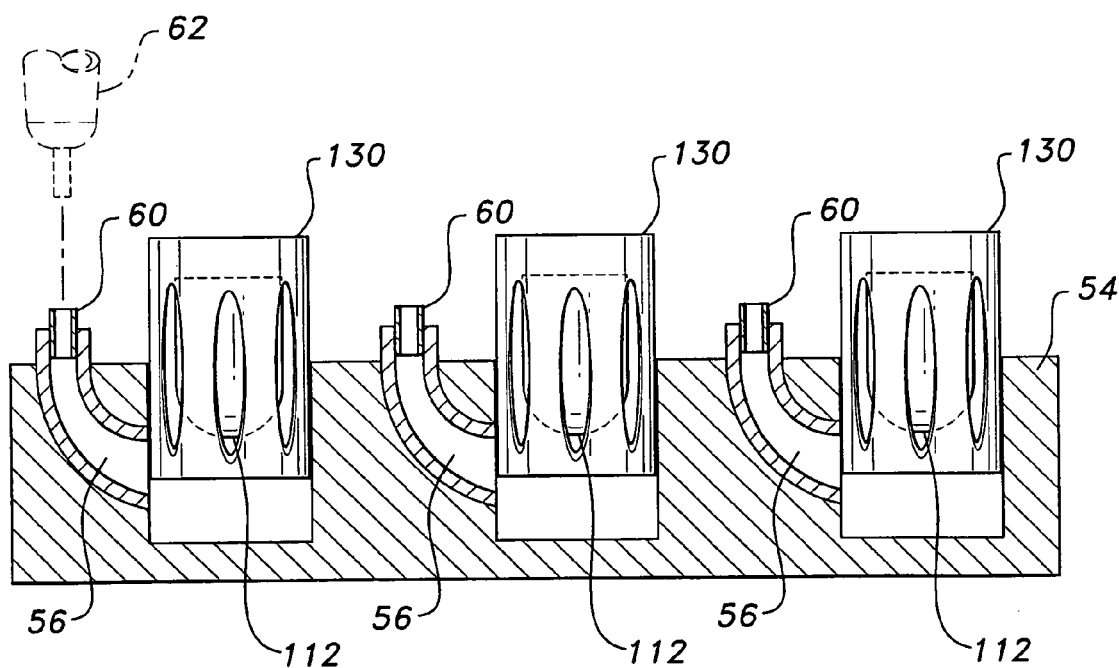
FIG. 5 is a side view of a plurality of removable and fillable heads of a bioinjection device according to the present invention.
Figure 6B:
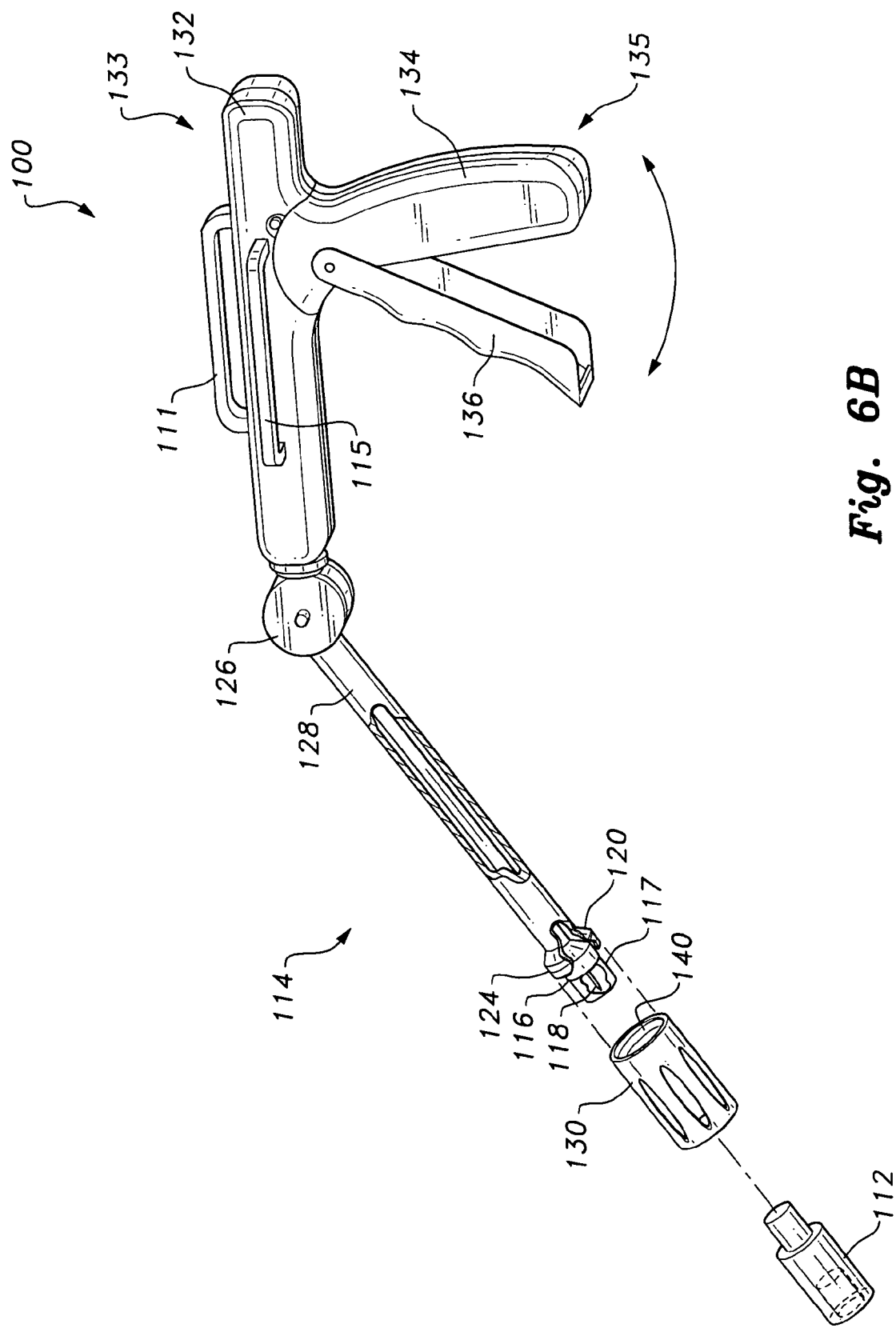
FIG. 6B is a perspective view of another alternative embodiment of the bioinjection device according to the present invention.

As shown in FIG. 5, the removable retaining members 130 may be stored and filled within a tray 54. In order to allow for quick insertion and replacement of cartridges 112, cartridges 112 may be positioned within retaining members 130, as shown. Tray 54 preferably includes a plurality of channels 56 for filling of cartridges 112 within the stored retaining members 130. A syringe 62 or other supply of medicament may be applied to ports 60, which cover and seal channels 56, allowing the medicament to be transferred to the cartridges 112. Communication with, and filling of, cartridges 112 may be accomplished through any suitable fluid transfer mechanism.

Figure 8:
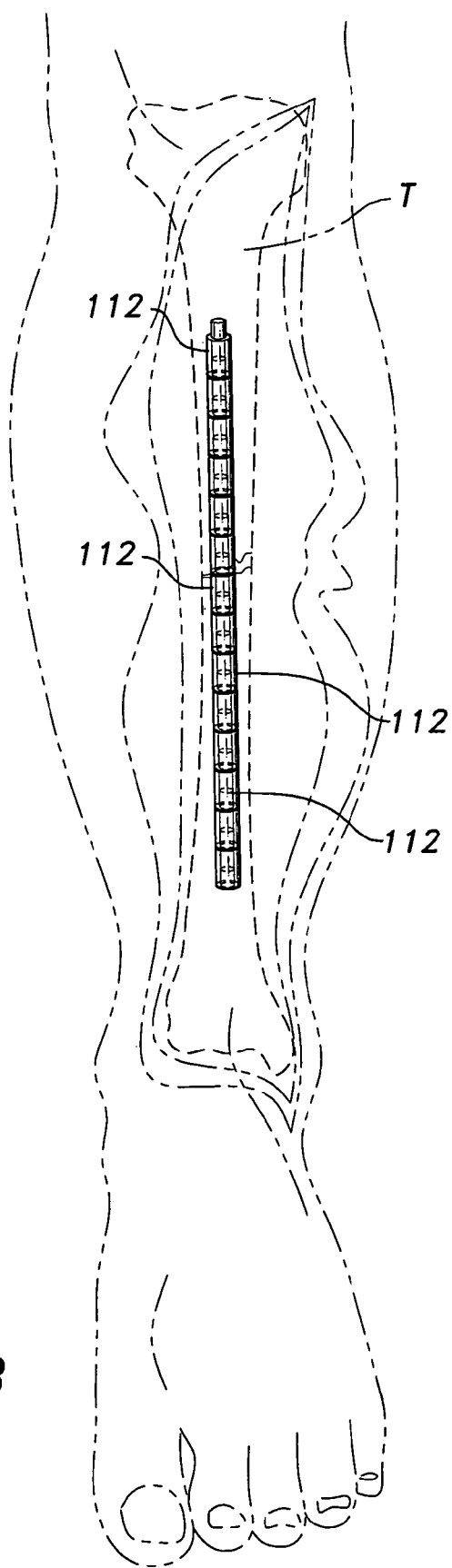
FIG. 8 is a front view of a human leg broken away to show the bone implants of FIG. 7 inserted within a channel formed within a bone.

FIG. 8 illustrates this stacked implantation within a channel C formed within an exemplary tibia T. Such channels C are often formed from the talus to the knee during the implantation of rods and the like in tibial reconstruction. The device 100 of FIG. 6 allows for easy insertion of multiple implants 112 within channel C after removal of such a rod.

Figure 10:
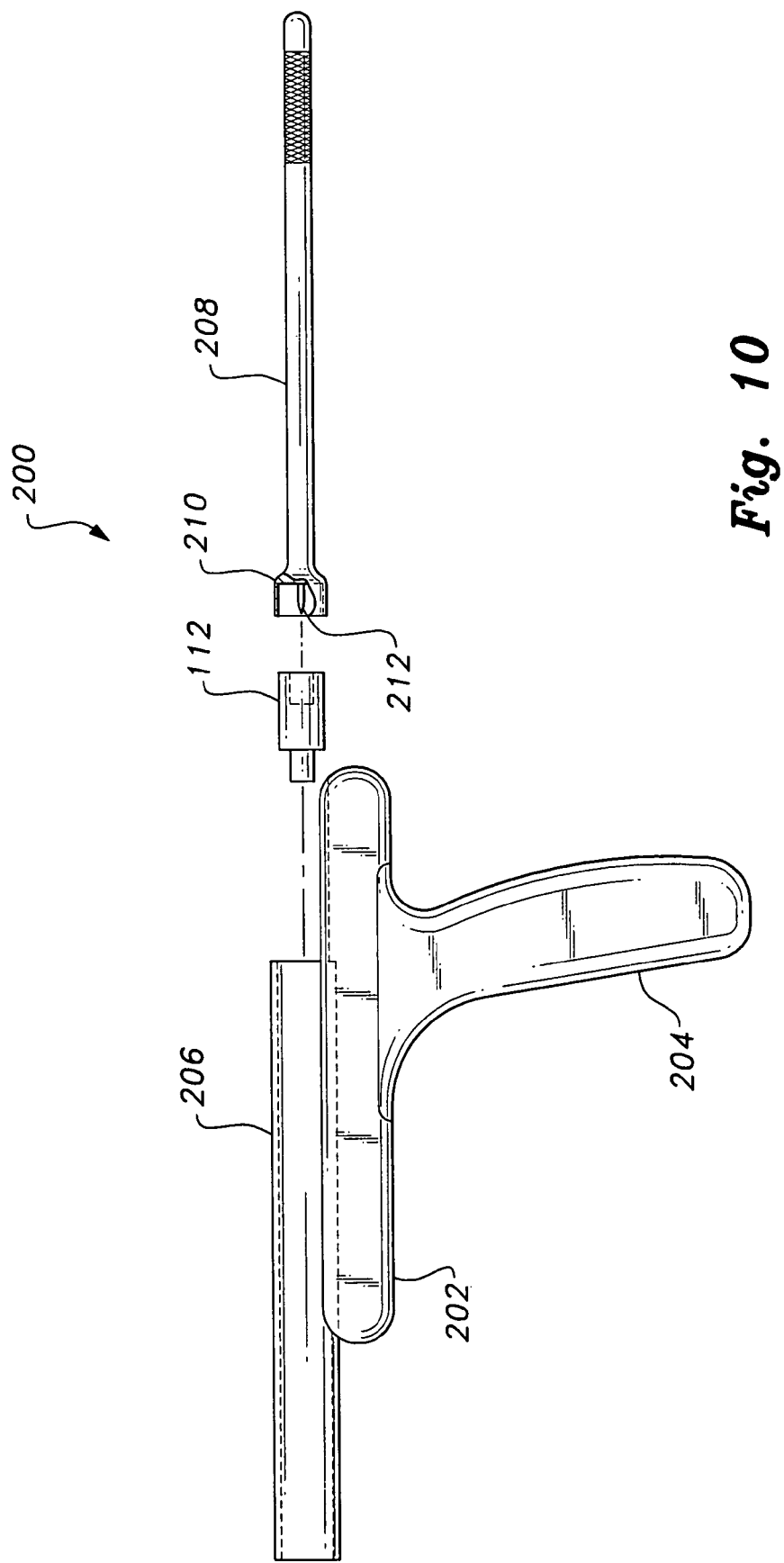
FIG. 10 is a side view of another alternative embodiment of the bioinjection device according to the present invention.

In the alternative embodiment of FIG. 10, device 200 allows for manual insertion and operation of the implant 112. A gripping handle portion 204 is secured to a lower surface of mount 202. Hollow insertion tube 206 is mounted on a front portion of the upper surface of mount 202, as shown. The rear portion of the upper surface of mount 202 may have a groove, ridge or other means for slidably holding implant 112. A plunger 208 is provided, with plunger 208 having a gripping, rear portion and a front portion terminating in a plunger head 210, with needle 212 being positioned centrally therein. In operation, the user loads an implant 112 onto the rear, upper surface of mount 202, as shown, and pushes implant 112 through tube 206, for insertion, with plunger head 210 pushing implant through tube 206 and needle 212 piercing the rear end of implant 112, as described above.

It is to be understood that the present invention is not limited to the embodiments described above, but encompasses any and all embodiments within the scope of the following claims.

We claim:

1. A bioinjection device, comprising:
   a housing having an upper portion and a lower gripping portion, the lower gripping portion having a handle member and a trigger member, the trigger member being pivotally attached to the handle member, the upper portion of the housing having an open interior region defined therein;

a shaft slidably mounted in the open interior region of the upper portion of the housing, the shaft having a channel formed therethrough, the shaft having opposed forward and rear ends;

at least one lever arm having first and second ends, the first end being attached to the rear end of the shaft, the second end being attached to the trigger member so that rotation of the trigger member with respect to the handle member drives sliding translation of the shaft with respect to the upper portion of the housing;

a needle slidably received within the channel formed through the shaft, the needle having opposed front and rear ends, the rear end of the needle being attached to the at least one lever arm so that rotation of the trigger member with respect to the handle member drives forward sliding translation of the needle with respect to the upper portion of the housing and the shaft;

a retaining member having opposed front and rear ends, the front end being open, the rear end being attached to the upper portion of the housing, the rear end of the retaining member and the forward portion of the upper portion having an opening formed therein so that the forward end of the shaft and the front end of the needle selectively and slidably project therethrough and into an open interior region of the retaining member; and a bone implant having an outer shell and a medicament disposed in the outer shell, the bone implant being releasably disposed in the open interior region of the retaining member, the forward end of the shaft contacting the bone implant, whereby actuation of the trigger member causes the shaft and the needle to slide forward, the shaft pushing the bone implant out of the retaining member for deployment into a bone, the needle piercing the outer shell to release the medicament.

2. The bioinjection device as recited in claim 1, wherein said retaining member is releasably attached to the upper portion of said housing.

3. The bioinjection device as recited in claim 1, wherein the lower gripping portion of said housing is selectively rotatable with respect to the upper portion of said housing.

4. The bioinjection device as recited in claim 3, further comprising an upper handle mounted on said housing.

5. The bioinjection device as recited in claim 4, further comprising a side handle mounted on said housing.

6. The bioinjection device as recited in claim 1, wherein said bone implant has opposed forward and rear ends, the rear end being formed from a membranous material so that said needle pierces the membranous material to release the medicament.

7. The bioinjection device as recited in claim 6, wherein the forward end of said bone implant forms an engaging member and the rear end has a recess defined therein so that a plurality of said bone implants may be stacked together with the engaging member of one of said bone implants being received within a corresponding recess of an adjacent one of said bone implants.

8. A bioinjection device, comprising:

a housing having an upper portion and a lower gripping portion, the upper portion of the housing having an open interior region defined therein;

a shaft slidably disposed in the open interior region of the upper portion of the housing, the shaft having a channel formed therethrough, said shaft having opposed forward and rear ends;

means for selectively driving sliding translation of the shaft with respect to the upper portion of the housing;

a needle slidably received within the channel formed through the shaft, the needle having opposed front and rear ends;

means for selectively driving sliding translation of the needle with respect to the upper portion of the housing and the shaft;

a retaining member having opposed front and rear ends, the front end being open, the rear end being attached to the upper portion of the housing, the rear end of the retaining member and the forward portion of the upper portion having an opening formed therein so that the forward end of the shaft and the front end of the needle selectively and slidably project the opening into the retaining member; and a bone implant having an outer shell and a medicament disposed in the outer shell, the bone implant being releasably disposed in the retaining member, the forward end of the shaft contacting the bone implant, whereby selective forward translation of the shaft and the needle causes the shaft to push the bone implant out of the retaining member for deployment into a bone, the needle piercing the outer shell to release the medicament.

9. The bioinjection device as recited in claim 8, wherein the lower gripping portion of said housing includes a handle member and a trigger member, the trigger member being pivotally attached to the handle member.

10. The bioinjection device as recited in claim 9, wherein the lower gripping portion is pivotal with respect to the upper portion.

11. The bioinjection device as recited in claim 9, wherein said means for selectively driving sliding translation of said shaft with respect to the upper portion of said housing comprises at least one lever arm having first and second ends, the first end being attached to the rear end of the shaft, the second end being attached to the trigger member so that rotation of the trigger member with respect to the handle member drives sliding translation of said shaft with respect to the upper portion of said housing.

12. The bioinjection device as recited in claim 11, wherein the rear end of said needle is attached to the at least one lever arm so that rotation of the trigger member with respect to the handle member drives forward sliding translation of said needle with respect to the upper portion of the housing and the shaft.

13. The bioinjection device as recited in claim 12, wherein said retaining member is releasably attached to the upper portion of said housing.

14. The bioinjection device as recited in claim 8, further comprising an upper handle mounted on said housing.

15. The bioinjection device as recited in claim 14, further comprising a side handle mounted on said housing.

16. The bioinjection device as recited in claim 8, wherein said bone implant has opposed forward and rear ends, the rear end being formed from a membranous material so that said needle pierces the membranous material to release the medicament.

17. The bioinjection device as recited in claim 16, wherein the forward end of said bone implant forms an engaging member and the rear end has a recess defined therein so that a plurality of said bone implants may be stacked together, with the engaging member of one of said bone implants being received within a corresponding recess of an adjacent one of said bone implants.

* * * * *